United States Patent [19]

Gosling et al.

[11] Patent Number: 5,138,112
[45] Date of Patent: Aug. 11, 1992

[54] PROCESS FOR CONVERTING A $C_2$-$C_6$ ALIPHATIC HYDROCARBON TO HIGH OCTANE TRANSPORTABLE FUEL

[75] Inventors: Christopher D. Gosling, Roselle, Ill.; Sabra L. Ehrhart, Lake Jackson, Tex.

[73] Assignee: UOP, Des Plaines, Ill.

[21] Appl. No.: 575,753

[22] Filed: Aug. 31, 1990

[51] Int. Cl.$^5$ .............................................. C07C 2/00
[52] U.S. Cl. .................................... 585/317; 585/310; 585/322; 585/418; 585/748; 585/752
[58] Field of Search ................ 585/310, 700, 752, 737, 585/940, 322, 317, 407, 418, 747, 748, 750

[56] References Cited

U.S. PATENT DOCUMENTS

| | | | |
|---|---|---|---|
| 3,843,740 | 10/1974 | Mitchell et al. | 260/673 |
| 4,704,496 | 11/1987 | Paparizos et al. | 585/500 |
| 4,783,575 | 11/1988 | Schmidt et al. | 585/748 |
| 4,834,866 | 5/1989 | Schmidt | 585/737 |
| 4,861,930 | 8/1989 | Cottrell et al. | 585/317 |

Primary Examiner—Anthony McFarlane
Attorney, Agent, or Firm—Thomas K. McBride; John G. Tolomei

[57] ABSTRACT

A combination process for the conversion of $C_2$-$C_6$ aliphatic hydrocarbons into easily transportable hydrocarbons of greater molecular weight. The combination process comprises converting the $C_2$-$C_6$ aliphatic hydrocarbons to aromatic hydrocarbons in a dehydrocyclodimerization reaction zone after which the aromatic product is isomerized in the presence of hydrogen from the dehydrocyclodimerization reaction step to produce transportable aliphatic hydrocarbons.

11 Claims, 1 Drawing Sheet

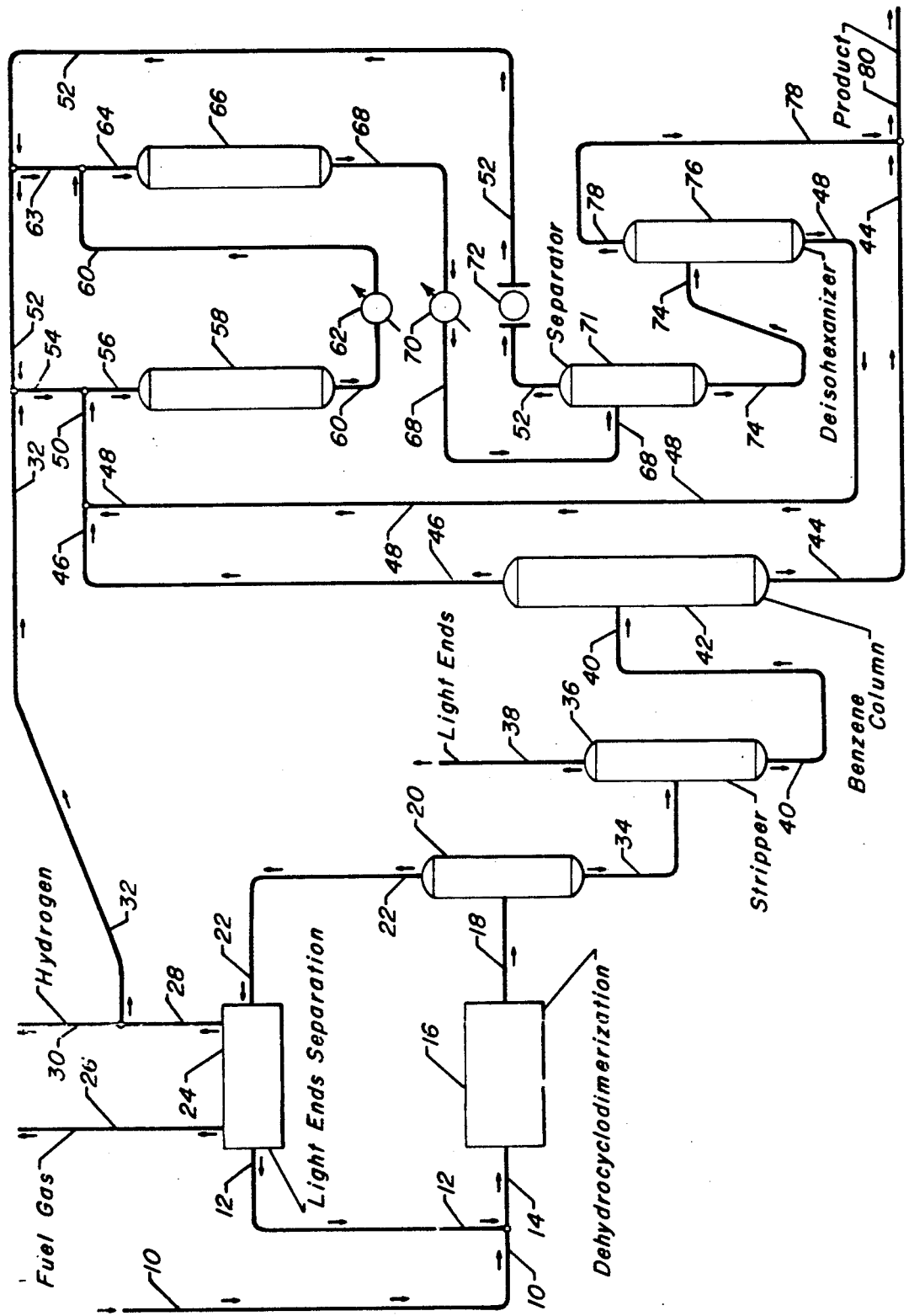

PROCESS FOR CONVERTING A C$_2$-C$_6$ ALIPHATIC HYDROCARBON TO HIGH OCTANE TRANSPORTABLE FUEL

BACKGROUND OF THE INVENTION

The present invention relates to a process for the conversion of light hydrocarbons that are typically volatile at standard conditions of temperature and pressure into hydrocarbons that are readily transportable at standard conditions.

In many remote areas of the world, light hydrocarbons are extracted from the earth along with crude oil. In these remote areas, the need for such hydrocarbons is non-existent. Recovered hydrocarbons must be transported to refineries and the like by pipelines or by ship. This poses a problem where light hydrocarbons such as C$_2$-C$_6$ aliphatic hydrocarbons are involved. Such hydrocarbons are not readily transportable and typically require special handling in specially designed ships.

Quite often, the amounts of these materials produced along with the difficulty in transporting these materials to a market by pipeline or vessel results in these valuable materials being flared as waste gases or reinjected back into the well. One approach that has been taken to eliminate this problem is to convert these volatile, low molecular weight hydrocarbons into higher molecular weight hydrocarbons which are readily transportable via the crude pipelines to markets. One such process for upgrading light hydrocarbons is the dehydrocyclodimerization process.

The dehydrocyclodimerization process produces a highly aromatic product from a feedstock comprising C$_2$-C$_6$ aliphatic hydrocarbons. Two relatively significant by-product streams comprising hydrogen, and C$_1$-C$_2$ hydrocarbons are also produced. In remote areas of the world and in the absence of refinery processes requiring hydrogen, the hydrogen and light hydrocarbon by-products must be disposed of typically by burning. Hydrogenation of the aromatic product has been used to maximize the amount of transportable products obtained from a light volatile hydrocarbon feed while minimizing the production of unusable light by-products. Hydrogenating the aromatic product has the disadvantage of reducing the octane of transportable product. Therefore, a process that would provide a high volume of transportable product having a high octane is very desirable. In addition, due to toxicity concerns it would also be desirable to eliminate benzene from the transported product.

INFORMATION DISCLOSURE

There are many patents relating to the upgrading of a light hydrocarbon feedstock into a transportable product. However, none of the processes known in the prior art is directed towards obtaining a high liquid volume yield having a high octane by first converting the light hydrocarbons into aromatic hydrocarbons followed by the saturation, decyclization and isomerization of product aromatics in an isomerization zone.

U.S. Pat. No. 4,704,496 discloses a process for converting light hydrocarbons into transportable materials by reacting the hydrocarbons with oxide initiators such as nitrogen oxides. However, this process does not use a solid catalyst. In addition, the '496 process produces some aromatic hydrocarbons which would normally be hydrogenated in the instant invention to produce a product with a higher liquid volume yield.

Processes for aromatizing light volatile hydrocarbons are well known. For example, U.S. Pat. No. 3,843,740 describes a process for aromatizing a hydrocarbon feed in the presence of a two-catalyst reaction system. In addition, a process for producing aromatics from LPG is described in an article "Process Makes Aromatics from LPG" by J. R. Mowry et al. in the *Oil and Gas Journal*, Vol. 83, No. 48, pp. 128-131 (Dec. 2, 1985). The article describes how aromatics can be produced from LPG in a single process. The above references, like most describing processes for upgrading LPG to aromatics, have as their goal the production of aromatics and not the maximization of the product liquid volume yield.

U.S. Pat. No. 4,861,930 teaches the direct hydrogenation of an aromatic and hydrogen containing process stream to maximize process weight and volume yields. The process stream is the product from a process for the aromatizing light volatile hydrocarbons. Although the '930 process increases the volume of liquid product, it does not provide a relatively higher octane product.

U.S. Pat. No. 4,783,575 teaches that an isomerization zone can be used to saturate and decyclize isomerization feedstocks that contain less than 30 wt. % aromatic hydrocarbons. There is no suggestion in the reference that such a process may be employed to produce isoalkane hydrocarbons from a principally aromatic feedstream.

BRIEF SUMMARY OF THE INVENTION

An object of this invention is to provide a novel hydrocarbon conversion process for the production of high octane transportable hydrocarbons from a feedstock comprising C$_2$-C$_6$ hydrocarbons.

The process utilizes two consecutive reaction zones wherein the first reaction zone is a dehydrocyclodimerization reaction zone and the second reaction zone is an isomerization reaction zone. The process produces a product with a larger weight and volume percent of transportable hydrocarbon products than are produced by conventional single step light hydrocarbon upgrading processes and a higher octane than is produced when the effluent of the upgraded product is hydrogenated alone. As an additional advantage of this process, the high octane product is also benzene free.

Accordingly, a broad embodiment of the present invention is directed towards a novel hydrocarbon conversion process for producing naphthenic hydrocarbons from a C$_2$-C$_6$ aliphatic hydrocarbon feedstock. The process comprises the steps of passing a hydrocarbon feedstock comprising at least one C$_2$-C$_6$ aliphatic hydrocarbon into a dehydrocyclodimerization reaction zone. The dehydrocyclodimerization reaction zone contains a dehydrocyclodimerization catalyst and is operated at dehydrocyclodimerization conditions sufficient to produce a reaction zone effluent stream comprising aromatic hydrocarbons and hydrogen. The entire dehydrocyclodimerization reaction zone effluent stream is next passed into an isomerization reaction zone as the isomerization zone feedstock. The isomerization reaction zone contains an isomerization catalyst and is operated at isomerization reaction conditions sufficient to convert a majority of the aromatic hydrocarbons in the isomerization reaction zone feedstock into isoalkanes. Finally, the hydrocarbon product of the isomerization reaction zone is separated and recovered as desired.

In a preferred embodiment, the instant process is useful for producing isoalkane hydrocarbons from a feedstock comprising $C_2$–$C_6$ aliphatic hydrocarbons by first passing a $C_2$–$C_6$ aliphatic hydrocarbon feedstream that has been preheated by contact with the dehydrocyclodimerization reaction zone effluent stream in a heat exchange means into a dehydrocyclodimerization reaction zone. The dehydrocyclodimerization reaction zone contains a catalyst comprising a ZSM-5 zeolite component, a phosphorus-containing alumina component, and gallium. The reaction zone is operated at dehydrocyclodimerization reaction conditions including a temperature of from 400°–600° C., a pressure of from 0.25 to 10 atmospheres, and a liquid hourly space velocity of from 0.5 to 5 hr.$^{-1}$. The dehydrocyclodimerization reaction zone effluent stream produced from the dehydrocyclodimerization reaction zone comprises hydrogen, methane, ethane, ethylene, $C_3$–$C_5$ aliphatic hydrocarbons, and $C_6+$ aliphatic and aromatic hydrocarbons. The dehydrocyclodimerization reaction zone effluent stream is passed to a separator for the separation of benzene and lower boiling hydrocarbons from the dehydrocyclodimerization reaction zone effluent into an isomerization zone feed and the reproduction of an aromatics stream comprising $C_7$ and higher boiling hydrocarbons. The isomerization zone feed is passed into an isomerization reaction zone. The isomerization reaction zone contains an isomerization catalyst comprising platinum or a Group VIII metal component on alumina and a chloride compound. The isomerization reaction zone is operated at isomerization reaction conditions including a temperature of from 65°–290° C. (150°–550° F.), a pressure of 700 to 3100 kPag (100 to 450 psig) and a liquid hourly space velocity of from 1.0 to 12 hr.$^{-1}$. The isomerization reaction zone product stream that is produced in the isomerization reaction zone contains little, if any, benzene and less hydrogen than the isomerization reaction zone feedstream. The isomerization reaction zone product stream is finally combined with an aromatics stream to produce a high octane transportable product.

DESCRIPTION OF THE DRAWING

The drawing is a simplified process flow diagram of a preferred embodiment of the invention. Various pumps, heat exchangers, valves, control instruments, minor vessels, fractionators, and the like have been eliminated or greatly reduced in order to clarify the drawings and thus implement the complete understanding of the present process. It is not intended that such omissions in the drawings or in the following discussion will unduly limit the present invention to the particular embodiments contained therein.

Referring now to the Figure, a hydrocarbon feedstream comprising $C_2$–$C_6$ aliphatic hydrocarbons is introduced into the process via line 10. This feedstream may be combined with recycle stream 12 comprising $C_2$–$C_5$ aliphatic hydrocarbons recovered in the separation zone of the process to produce a combined feedstream 14 to the dehydrocyclodimerization reaction zone 16. The effluent from dehydrocyclodimerization reaction zone 16 is taken by a line 18 and passed into a separator 20. Light hydrocarbons are taken overhead from the separator by a line 22 and passed to a light ends separator 24. Light ends separator 24 divides the separator overhead stream into the recycle stream 12 that comprises $C_2$–$C_4$ hydrocarbons, a fuel gas stream 26 comprising light noncondensible gases and a hydrogen stream 28. Hydrogen stream 28 is divided into a make-up hydrogen stream 32 and a net hydrogen stream 30 that is withdrawn from the process. The bottoms of separator 20, comprising $C_5$ and heavier hydrocarbons are removed by a line 34 and passed to a stripper 36. Additional light ends are taken overhead from stripper 36 by a line 38 and the remaining heavier hydrocarbons are taken as a bottoms stream 40 and passed to a benzene column 42. A bottoms stream 44 withdraws a benzene depleted stream from column 42. A line 46 takes benzene and lower boiling hydrocarbons into admixture with a recycle stream 48 to form an isomerization zone feed 50. Make-up hydrogen from line 32 and recycle hydrogen from a line 52 are combined in a line 54, the contents of which are mixed with line 50 and passed into a first isomerization reaction zone 58 by a line 56. The effluent from isomerization reaction zone 58 is taken by a line 60, cooled by a heat exchanger or steam generator 62, mixed with recycle hydrogen from a branch line 63 and passed into a second isomerization reaction zone 66 by a line 64. Effluent from isomerization reaction zone 66 is withdrawn by a line 68, cooled in a heat exchanger or steam generator 70 and passed to separator 71. Excess hydrogen from line 68 is flashed in separator 71, withdrawn overhead by line 52 and recompressed in a compressor 72 for supply to the isomerization reactors. Line 74 carries the remaining portion of the isomerization zone effluent stream into a deisohexanizer column 76. The recycle stream 48 comprising normal hexane and higher boiling hydrocarbons is withdrawn from the lower end of column 76 while the lighter hydrocarbons are taken overhead and combined with the aromatics carried by line 44 into a stream 80 that supplies a high octane transportable liquid product.

DETAILED DESCRIPTION OF THE INVENTION

This invention relates to a process for the production of transportable hydrocarbons from difficult-to-transport hydrocarbon feedstocks such as $C_2$–$C_6$ hydrocarbons. The process is especially useful in minimizing the volume of hydrogen produced in upgrading the volatile, difficult-to-transport hydrocarbons into more stable hydrocarbons. Because hydrogen remains incorporated into the molecular structure of the hydrocarbon molecules, the weight and liquid volume percent yield of $C_6+$ hydrocarbons typically exceeds that of conventional dehydrocyclodimerization processes.

One method to avoid costly shipping or disposal of light hydrocarbons is to upgrade the $C_2$–$C_6$ hydrocarbons on site into readily pumpable and shippable hydrocarbons such as aromatics. However, the conversion of $C_2$–$C_6$ aliphatic hydrocarbons into aromatic hydrocarbons via dehydrocyclodimerization results in large amounts of hydrogen being produced. In a typical refinery, such hydrogen would be useful in various heavy oil upgrading processes, but such hydrogen would be a waste product in an isolated crude production site.

The process of this invention is able to minimize the problem of waste hydrogen production while producing a transportable hydrocarbon product that can be used as a gasoline blending product without further processing. The instant process utilizes a dehydrocyclodimerization reaction zone in combination with an isomerization reaction zone. Such a process utilizes hydrogen in the transportable product while producing a high octane transportable product that can be used as a gasoline blending component without additional processing.

The first unit of the process of this invention is the dehydrocyclodimerization reaction zone. In the dehydrocyclodimerization reaction zone, $C_2$-$C_6$ aliphatic hydrocarbons are converted into aromatic hydrocarbons. The conversion of $C_2$-$C_6$ paraffins and olefins to aromatic hydrocarbons (dehydrocyclodimerization) may be expressed in terms of a three-stage process involving dehydrogenation, oligomerization, and aromatization reactions. While the reaction stages will be described as occurring sequentially, it is to be understood that all three reactions will take place simultaneously within the dehydrocyclodimerization reaction zone. The first reaction stage involves the dehydrogenation of paraffins to form olefins. Olefins may be derived from paraffins by the direct dehydrogenation of a paraffin to form the corresponding olefin and hydrogen or by carbon-carbon fission to produce lower alkanes and olefins. At temperatures thermodynamically favoring dehydrogenation (i.e., temperatures of about 500°-700° C.), the direct dehydrogenation reaction competes with the carbon-carbon fission reaction. At these temperatures and in the absence of a dehydrogenation catalyst, the predominant mechanism is fission of the carbon-carbon bond (C—C) which has a lower bond energy than the carbon-hydrogen bond (C—H). The higher the alkane, the greater the tendency toward carbon-carbon fission. In the case of propane, two decomposition reactions are possible, one leading to propylene and free hydrogen, the other to ethylene and methane, with the latter slightly predominating. In the case of butane, the predominant reaction is fission at the end of the carbon chain to produce propylene and methane, with the next predominant reaction being fission of the interior carbon atoms to produce ethane and ethylene. Only a minor amount of direct dehydrogenation resulting in butenes and free hydrogen takes place.

Ethylene, ethane, and methane are the least desirable products of the carbon fission reaction. Methane remains in the reactor system as a refractory product. In a desired reaction, ethane may be dehydrogenated to ethylene prior to oligomerization to larger hydrocarbons. This reaction however occurs slowly and due to the speed and frequency of the undesirable ethylene hydrogenation reaction, the dehydrogenation reaction does not substantially alter the ethane concentration in the reaction mixture. In fact, the concentration of ethane in the reaction mixture will increase with increasing reactor residence time due to the dominance of the ethylene hydrogenation reaction in comparison to the ethylene oligomerization or ethane dehydrogenation reactions. The ethylene carbon fusion reaction products as previously explained may be hydrogenated to ethane or oligomerized.

In the second stage of the conversion process, the olefins undergo oligomerization to produce cyclic naphthenes. The naphthenes are then dehydrogenated in the third stage of the conversion process to produce the corresponding aromatic compounds. The cyclic naphthenes include saturated cycloalkanes and unsaturated alicyclic compounds with the former usually predominating. The predominant cyclic naphthenes produced in the second stage are six-member cyclic rings substituted with one or two alkyl groups containing a total of 1 to 12 carbon atoms. These cyclic naphthenes are dehydrogenated to produce the corresponding aromatic hydrocarbons, e.g. benzene, toluene, ethylbenzene, xylenes, and other higher molecular weight alkyl benzenes.

The operating conditions which will be employed in the dehydrocyclodimerization reaction zone will, of course, vary depending on such factors as feedstock composition and desired conversion. A desired range of conditions for the dehydrocyclodimerization of $C_2$-$C_6$ aliphatic hydrocarbons to aromatics include a temperature from about 350° to about 650° C., a pressure from about 0.1 to about 20 atmospheres, and a liquid hourly space velocity from about 0.2 to about 10 hr.$^{-1}$. The preferred process conditions are a temperature in the range from about 400° to about 600° C., a pressure in or about the range from 0.25 to 10 atmospheres, and a liquid hourly space velocity of between 0.5 and 5 hr.$^{-1}$. It is understood that as the average carbon number of the feed increases, a temperature in the lower end of temperature range is required for optimum performance and, conversely, as the average carbon number of the feed decreases, the higher the required reaction temperature.

The feedstream to the dehydrocyclodimerization process is defined herein as those streams introduced into the dehydrocyclodimerization reaction zone which provide reactants for the three dehydrocyclodimerization reactions mentioned hereinabove. Included in the feedstream are $C_2$-$C_6$ aliphatic hydrocarbons. By $C_2$-$C_6$ aliphatic hydrocarbons, it is meant that the feedstream may comprise one or more open, straight, or branched chain isomers having from about 2 to 6 carbon atoms per molecule. Furthermore, the hydrocarbons in the feedstock may be saturated or unsaturated. Preferably, the hydrocarbons, $C_3$ and/or $C_4$, are selected from isobutane, normal butane, isobutene, normal butene, propane, and propylene. Diluents, refractory or reactant in nature, may also be included in the feedstream. Examples of such diluents include hydrogen, nitrogen, helium, methane, argon, neon, CO, $CO_2$, $H_2O$ or its precursors. Water precursors are defined as those compounds which liberate $H_2O$ when heated to dehydrocyclodimerization reaction temperatures. Methane and hydrocarbons greater than $C_6$ aliphatic hydrocarbons may also be components of the feedstock of the instant invention. The methane component is generally but not always a refractory reactant. The $C_6+$ aliphatic components while participating in the reactions are more efficiently handled by isomerization. In any case, it is expected that the inclusion of such components in the feed will deterimentally affect the reaction kinetics of the dehydrocyclodimerization reaction.

According to the present invention, the $C_2$-$C_6$ aliphatic hydrocarbon feedstream is contacted with the catalytic composite in a dehydrocyclodimerization reaction zone maintained at dehydrocyclodimerization conditions. This contacting may be accomplished by using a catalytic composite in a fixed bed system, a moving bed system, a fluidized bed system, or in a batch-type operation; however, in view of the fact that attrition losses of the valuable catalyst should be minimized and of the well-known operational advantages, it is preferred to use either a fixed bed catalytic system or a dense phase moving bed system such as is shown in U.S. Pat. No. 3,725,249. It is contemplated that in the case where a fixed bed catalytic system is employed to accomplish the process of the present invention that the catalyst of this invention may be contained in one or more fixed bed reactors.

In a fixed bed system or in a dense-phase moving bed system, the feedstream is preheated by any suitable heating means to the desired reaction temperature and then passed into a dehydrocyclodimerization zone containing a bed of the catalytic composite of this invention. It is, of course, understood that the dehydrocyclodimerization zone may be one or more separate reactors with suitable means therebetween to assure that the desired conversion temperature is maintained at the entrance to each reactor. It is also important to note that the reactants may be contacted with the catalyst bed in either upward, downward, or radial flow fashion, with the latter being preferred. In addition, the reactants may be in the liquid phase, admixed liquid-vapor phase, or a vapor phase when they contact the catalyst, with the best results obtained in the vapor phase. The dehydrocyclodimerization system then preferably comprises a dehydrocyclodimerization zone containing one or more fixed or dense-phase moving beds of a dehydrocyclodimerization catalytic composite.

In a multiple bed system, the dehydrocyclodimerization zone may be one or more separate reactors with suitable heating means therebetween to compensate for any heat loss encountered in each catalyst bed. Specific to the dense-phase moving bed system, it is common practice to remove catalyst from the bottom of the reaction zone, regenerate it by conventional means known to the art, and then return it to the top of the reaction zone.

The dehydrocyclodimerization catalyst useful in the present process may be any catalyst of the prior art known to have the capability to convert light aliphatic hydrocarbons into aromatic hydrocarbons. Examples of such catalysts are disclosed in U.S. Pat. Nos. 4,499,315 and 4,720,602. Additionally, it should be noted that the dehydrocyclodimerization process need not be accomplished in a single reaction zone but may be replaced by any combination process that is capable of producing an aromatic-containing hydrocarbon product from a light aliphatic hydrocarbon product such as disclosed in U.S. Pat. No. 4,705,908 or Canadian Patent 1,237,447. However, a single reaction system containing a single dehydrocyclodimerization catalyst is preferred.

The preferred catalyst useful in the dehydrocyclodimerization reaction zone of the instant process comprises a phosphorus-containing alumina, a Group IIB, IIIB, or IVB metal component from the Periodic Table of the Elements, especially a gallium component, and a crystalline aluminosilicate zeolite having a silicato-alumina ratio of at least 12. The preferred catalyst is further characterized in that the crystalline aluminosilicate is ZSM-5 and is present in an amount ranging from 35 to 59.9 wt. %. In addition, the most preferred catalyst comprises from 0.1 to 5 wt. % gallium and from 40 to 60 wt. % of a phosphorus-containing alumina component. Such a catalyst is described in U.S. Pat. No. 4,636,483 which is incorporated herein by reference.

The effluent from the dehydrocyclodimerization reaction zone typically comprises hydrogen, methane, ethane, ethylene, $C_3$–$C_5$ hydrocarbons and $C_6+$ plus aliphatic and aromatic hydrocarbons. At least a portion of these hydrocarbons are transferred to the isomerization zone of this invention. All of the dehydrocyclodimerization reaction zone effluent can be transferred to the isomerization zone in the practice of this invention; however, it is preferable to first separate light ends and $C_7+$ aromatic and aliphatic hydrocarbons from the feed that enters the isomerization zone. Excessive amounts of light end materials interfere with the operation of the isomerization zone by increasing the mass flow through the reaction zone. Most of the $C_7$ and higher hydrocarbons will be aromatics that already have a high octane rating and are not believed to pose the same environmental hazards as benzene. Therefore, the preferred arrangement of this invention will pass the dehydrocyclodimerization zone effluent to one or more separation zones before it enters the isomerization zone.

One such separation zone will recover light ends and separate the hydrogen from the light ends for use as a feed in the isomerization zone. The Figure shows the preferred form for this separation zone where the dehydrocyclodimerization effluent enters a first separator in the form of a separation column. This separator will be designed to flash at least $C_3$ and lower boiling hydrocarbons overhead. Depending on the operation of the isomerization zone this separator may also be designed to separate $C_4$ and lighter hydrocarbons where it is desirable to minimize the presence of $C_4$'s in the final product.

The overhead stream comprising the rough cut of the light ends from the dehydrocyclodimerization effluent enters a light ends recovery section. The light ends recovery section typically uses an absorber system or a cryogenic separation to recover a hydrogen stream at a purity of at least 90%. Additional stages of separation remove the methane, ethylene and some ethane which is ordinarily recovered for use as fuel gas. Any remaining $C_2$ and higher hydrocarbons are recycled to the dehydrocyclodimerization reaction zone with the incoming feed.

In the preferred configuration of the drawing the simple flash separation of the dehydrocyclodimerization effluent is followed by a stripping of the flash separator bottoms in a stripper. The stipper removes additional noncondensible and $C_3$ hydrocarbons from the relatively heavy portion of the dehydrocyclodimerization effluent. The stripper may also be designed to remove $C_4$ hydrocarbons from the heavy hydrocarbon cut. The light ends removed overhead from the stripper are typically used for fuel gas.

The stabilized bottoms stream may be passed directly to the isomerization zone of this invention or passed to an additional separation zone for the recovery of high octane aromatics. An important aspect of this invention is the saturation of benzene in the isomerization zone. Accordingly, the separation zone will be designed to carry essentially all of the benzene to the isomerization zone. For this reason the separation zone is preferably in the form of a benzene column that separates benzene and lower boiling hydrocarbons from a heavy aromatic cut. Separating out the aromatic cut reduces the feed rate to the isomerization reaction zone while preserving high octane aromatics that are already in a transportable form and can be combined with the effluent from the isomerization zone to raise the octane of the transportable product.

All of the remaining components of the dehydrocyclodimerization effluent, following any separation, enter the isomerization zone. The isomerization can take on many forms but, in addition to providing an isomerization function, is specifically designed to provide a saturation and ring opening function for the removal of benzene. Most isomerization zones with ordinary isomerization catalysts can provide the saturation and ring opening function. Suitable catalysts will include a Group VIII metal component to promote saturation of any unsaturated compounds. Suitable catalysts will also have an acid function to promote ring opening and isomerization.

The preferred catalyst for this the isomerization zone is a chlorided platinum alumina catalyst. The alumina is preferably an anhydrous gamma-alumina with a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be most suitable for this process. The catalyst will contain from about 0.1 to 0.25 wt. % of the platinum. Other platinum group metals may be present in a concentration of from 0.1 to 0.25 wt. %. The platinum component may exist within the final catalytic composite as an oxide or halide or as an elemental metal. The presence of the platinum component in its reduced state has been found most suitable for this process. The chloride component termed in the art "a combined chloride" is present in an amount from about 2 to about 10 wt. % based upon the dry support material. The use of chloride in amounts greater than 5 wt. % have been found to be the most beneficial for this process. The inorganic oxide preferably comprises alumina and more preferably gamma-alumina, eta-alumina, and mixtures thereof.

There are a variety of ways for preparing the catalytic composite and incorporating the platinum metal and the chloride therein. In one such method the catalyst is prepared by impregnating the carrier material through contact with an aqueous solution of a water-soluble decomposable compound of the platinum group metal. For best results, the impregnation is carried out by dripping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of halogen must be incorporated into the catalyst by the addition or formation of aluminum chloride to or on the platinum-aluminum catalyst base. An alternate method of increasing the halogen concentration in the final catalyst composite is to use an aluminum hydrosol to form the aluminum carrier material such that the carrier material also contains at least a portion of the chloride. Halogen may also be added to the carrier material by contacting the calcined carrier material with an aqueous solution of the halogen acid such as hydrogen chloride.

It is generally known that high chloride platinum-alumina catalysts of this type are highly sensitive to sulfur and oxygen-containing compounds. Therefore, the use of such catalysts requires that the feedstock be relatively free of such compounds. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$–$C_5$ oxygenates, that can decompose to form water, can only be tolerated in very low concentrations. In general, this requires a limitation of oxygenates in the feed to about 0.1 ppm or less. The feedstock may be treated by any method that will remove water and sulfur compounds. Sulfur may be removed from the feedstream by hydrotreating. A variety of commercial dryers are available to remove water from the feed components. Adsorption processes for the removal of sulfur and water from hydrocarbon streams are also well known to those skilled in the art.

Operation of the reaction zone with the preferred chlorided platinum-alumina catalyst also requires the presence of a small amount of an organic chloride promoter. The organic chloride promoter serves to maintain a high level of active chloride on the catalyst as low levels are continuously stripped off the catalyst by the hydrocarbon feed. The concentration of promoter in the reaction zone is maintained at from 30 to 300 ppm. The preferred promoter compound is carbon tetrachloride. Other suitable promoter compounds include oxgen-free decomposable organic chlorides such as propyldichloride, butylchloride, and chloroform to name only a few of such compounds. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

The catalytic composites that can be used in this process also include crystalline alumino-silicates or crystalline zeolites. Suitable catalyst compositions of this type will exhibit selective and substantial isomerization activity under the operating conditions of the process. As a general class, suitable catalysts of this type comprise crystalline zeolitic molecular sieves having an apparent pore diameter large enough to adsorb neopentane, a silica-alumina molar ratio, $SiO_2/Al_2O_3$, of greater than 3; less than 60 and preferably between 15 and 30. In a preferred form, the zeolite will also contain an equivalent percent alkali metal cations and will have those $AlO_4$-tetrahedra not associated with alkali metal cations either not associated with any metal cations or associated with divalent or other polyvalent metal cations. Usually the molecular sieve is a mordenite molecular sieve, which is essentially in the acid form or is converted to the acid form. Particularly preferred catalysts for the isomerization zone are disclosed in detail in U.S. Pat. Nos. 3,442,794 and 3,836,597.

The catalyst composition can be used alone or can be combined with a porous inorganic oxide diluent as a binder material. The hydrogenation agent can be carried either on the zeolitic component and/or on the binder. A wide variety of inorganic oxide diluent materials are known in the art some of which also exhibit hydrogenation activity. Therefore, when referring to inorganic diluent having a hydrogenation agent thereon, this expression includes both diluents which have no hydrogenation activity themselves and carry a separate hydrogenation agent as well as those diluents which are themselves hydrogenation catalysts. Suitable oxides which exhibit inherent hydrogenation activity are the oxides of chromium, molybdenum and tungsten. Preferably, the diluent material will also not possess catalytic cracking activity that is higher than the crystalline alumino-silicate component of the isomerization catalyst composition. Suitable oxides of this type include aluminas, silicas, the oxides of metals of Groups III, IVA and IVB of the Mendeleev Periodic Table and cogels of silica and oxides of the metals of Groups III, IVA and IVB. Especially preferred oxides are aluminum, zirconium, titanium, thoria and combinations thereof. Other suitable binders include alumino-silicate clays such as kaoline, attapulgite, sepiolite, polygarskite, bentonite and montmorillonite, when rendered in a pliant plastic-like condition by intimate admixture with water, particularly when the clays have not been acid washed to remove substantial quantities of alumina.

Another catalyst composition for use in the present invention comprises a Group VIII noble metal, a hydrogen form crystalline alumino-silicate, and a refractory inorganic oxide with said catalyst composition having a surface area of at least 580 $M^2/g$. Significant improvements in isomerization performance are realized when the surface area of the catalytic composition is at or above 580 $M^2/g$. The Group VIII noble metal that is again incorporated into the catalytic composite to supply the hydrogenation-dehydrogenation function and the preferred Group VIII noble metal is platinum. The Group VIII noble metal is present in an amount from about 0.1 to about 5% by weight of the composite and preferably in an amount of at least about 0.15% by weight, but not over 0.5by weight. The catalytic composite may also contain a catalytically effective amount of a promoter metal such as tin, lead, germanium, cobalt, nickel, iron, tungsten, chromium, molybdenum, bismuth, indium, gallium, cadminum, zinc, uranium, copper, silver, gold, tantalum, or one or more of the rare earth metals and mixtures thereof. The hydrogen form silica-alumina has either a three-dimensional or channel-pore-structure crystal lattice framework. The three-dimensional alumino-silicates include both synthetic and naturally occurring silica aluminas, such as, the faujasites which include X-type, Y-type, ultrastable-Y and the like. L-type, omega-type, and mordenite are examples of the channel-pore-structure crystalline alumino-silicates. Mordenite in either naturally occurring or synthetic form are preferred, particularly with a silica to alumina ratio of at least 16:1. The hydrogen form alumino-silicate may be present in an amount within the range of 50 to about 99.5 wt. %, preferably within the range of 75 to about 95 wt. %, and the refractory inorganic oxide may be present in an amount within the range of from 0.5 to about 50 wt. %. The inorganic oxide preferably comprises alumina and more preferably gamma-alumina, eta-alumina and mixtures thereof.

Operating conditions within the isomerization zone are selected to maximize the production of isoalkane product from the feed components. Temperatures within the reaction zone will usually range from about 40°–260° C. (105°–500° F.). Lower reaction temperatures are preferred for purposes of isomerization conversion since they favor isoalkanes over normal alkanes in equilibrium mixtures. However, maximizing ring opening sometimes requires temperatures in excess of those that are most favorable from an equilibrium standpoint. For example, when the feed mixture is primarily $C_5$ and $C_6$ alkanes, temperatures in the range of 65° to 160° C. are desired from a normal-isoalkane equilibrium standpoint, but the preferred temperature range for this invention lies between 100°–200° C. When it is desired to isomerize significant amounts of $C_4$ hydrocarbons, higher reaction temperatures are required to maintain catalyst activity. Thus, when the feed mixture contains significant portions of $C_4$–$C_6$ alkanes, the most suitable operating temperatures for ring opening and isoalkane equilibrium coincide and in the range from 145°–225° C. Excessive reaction zone temperatures should be avoided since they lower the equilibrium concentration of isoalkanes and promote cracking of and the production of light materials. The reaction zone may be maintained over a wide range of pressures. Pressure conditions in the isomerization of $C_4$–$C_6$ paraffins range from 700 kPag to 3100 kPag. Higher pressures favor ring opening, therefore, the preferred pressures for this process are in the range of from 1500 kPag to 3000 kPag. The feed rate to the reaction zone can also vary over a wide range. These conditions include liquid hourly space velocities ranging from 0.5 to 12 hr.$^{-1}$, however, space velocities between 0.5 and 3 hr.$^{-1}$ are preferred.

The isomerization section can be arranged in any manner that facilitates its operation for the conversion of benzene to $C_5$ and $C_6$ isoparaffins. Preferably, the isomerization section will have at least two reaction zones with a first stage reactor and a second stage reactor in the reaction section. It is not necessary that the reaction be carried out in two reactors but the use of two reactors confer several benefits on the process. Typically a two reactor isomerization section uses the same catalyst distributed equally between the two reactors. The use of two reactors and specialized valving allows partial replacement of the catalyst system without taking the isomerization unit off stream. For the short periods of time during which replacement of catalyst may be necessary, the entire flow of reactants may be processed through only one reaction vessel while catalyst is replaced in the other. The use of two reaction zones also aids in maintaining lower catalyst temperatures. This is accomplished by having any exothermic reaction such as hydrogenation of aromatics or unsaturates performed in a first reaction vessel with the rest of the reaction carried out in a final reaction vessel at more favorable temperature conditions.

In the preferred two reactor system, the feedstock is mixed with a hydrogen containing gas stream before entering a first conversion zone. The gas stream should contain at least 50 wt. % of hydrogen. Preferably, the hydrogen-containing gas stream will have a hydrogen concentration greater than 75 wt. % hydrogen. Hydrogen producing processes from which the gas stream is obtained can contain relatively large amounts of light hydrocarbons. These light hydrocarbons are undesirable since their presence needlessly increases the mass volume through the first reactor and their relatively high vapor pressure can increase the loss of product in downstream separation facilities.

The gas stream is mixed with the feed in proportions that will usually produce a hydrogen to hydrocarbon ratio of 0.5-2 stdm$^3$/m$^3$. The first conversion zone of this invention can be operated with hydrogen concentrations as low as 0.4 stdm$^3$/m$^3$.

The feed is heated as necessary to achieve the desired reaction temperature and then enters the first conversion zone. Conditions within the first conversion zone typically include a temperature in the range of 190°–290° C. (375°–550° F.), a pressure of from 1200–3100 kPag (175–450 psig) and a liquid hourly space velocity of from 4–12. Typically, the reaction conditions are selected to keep the hydrocarbon feed in a vapor phase. The particular operating conditions within the first conversion zone will also be influenced by the makeup of the feedstream and the catalyst composition employed therein.

Temperatures within the second conversion zone will usually operate at somewhat lower temperatures and range from about 65°-280° C. (150°-536° F.). These lower temperatures are particularly useful in processing feeds composed of $C_5$ and $C_6$ paraffins where the lower temperatures favor equilibrium mixtures having the highest concentration of the most branched paraffins. When the feed mixture is primarily $C_5$ and $C_6$ paraffins temperatures in the range of from 65°-160° C. (150°-320° F.) are preferred. When it is desired to isomerize significant amounts of $C_4$ hydrocarbons, higher reaction temperatures are required to maintain catalyst activity. Thus, when the feed mixture contains significant portions of $C_4$-$C_6$ paraffins most suitable operating temperatures are in the range from 140°-235° C. (280°-455° F.). The second conversion zone may be maintained over the same range of pressures given for the first conversion zone. The feed rate to the second conversion zone may also vary over a wide range but will usually include liquid hourly space velocities that are lower than the first conversion zone and range from 0.5-10 hr.$^{-1}$, with space velocities of between 1 and 8 hr.$^{-1}$ being preferred. The hydrogen concentration in the second conversion zone may also be adjusted by the addition of hydrogen to the feed or to the second conversion zone.

In most cases the effluent from the second isomerization zone will enter a separation zone for the removal of light gases from the isoparaffin containing product stream. The light gases include hydrogen that was added to the feedstream entering the first conversion zone and any additional hydrogen that was added to the feed entering the second conversion zone. At minimum, the separation facilities divide the conversion zone effluent into a product stream comprising $C_4$ and heavier hydrocarbons and a gas stream which is made up of lighter hydrocarbons and hydrogen. Suitable designs for rectification columns and separator vessels are well known to those skilled in the art. $C_3$ and lighter hydrocarbons and any excess hydrogen from the second conversion zone are removed or returned to the process as part of the hydrogen gas stream.

In the preferred form of this invention the hydrogen is recompressed and returned to the isomerization zone. It is known in the art to simplify an isomerization zone process arrangement and avoid recycle facilities by maintaining a low hydrogen concentration in the isomerization reaction section. It is possible to practice this invention with an isomerization zone arranged in such a manner. In most cases, however, the isomerization section of this invention is operated with a relatively high hydrogen concentration in order to maximize the hyhydrogenation of the hydrocarbons, reduce catalyst fouling and provide a heat sink for the exothermic heat of reaction. As a result, recycle facilities for the recovery and return of hydrogen will usually be used in conjunction with this invention.

After removal of light ends, the isoparaffin containing product stream can be used directly as a high octane hydrocarbon stream that is ready for transport at normal transport conditions. In most cases, the product stream will be recombined with any higher aromatics that were separated from the feed to the isomerization reaction section. The only restraint on this operation is the lower octane value of the product due to the large amount of normal paraffins and cyclohexane that is present in the product. Therefore, the preferred form of this invention separates the lower octane normal paraffin and cyclohexane components from the stabilized isomerization zone effluent and recycles such components back to the isomerization zone.

An ordinary provision in the design of isomerization flow schemes is the use of one or more columns to recover lower octane paraffins for recycle to the isomerization zone. This invention may include one or more separation sections for the recovery of low octane $C_6$ hydrocarbons and the recycle of such hydrocarbons to the isomerization zone. Many arrangements for the isomerization of $C_5$ and $C_6$ isomerization zones use a deisohexanizer column to recover normal hexane and return it to the isomerization zone. In a preferred arrangement, this invention uses a deisohexanizer column to separate normal hexane and higher boiling hydrocarbons from the isomerization zone effluent stream. The use of a deisohexanizer column has the advantage of raising the octane of the transportable product and creating more liquid volume products. After separation of the isomerization effluent in the deisohexanizer or any other separation section, the high octane isomerization zone products are recovered and provide all or a part of the high octane transportable product. The total stream of high octane transportable product can include any heavier portion of the dehydrocyclodimerization reaction effluent that was not included in the isomerization zone feed.

EXAMPLE

The advantages of this invention over prior processes for the utilization of light hydrocarbon gas streams by the hydrogenation of dehydrocyclodimerization effluent are shown in the following examples. These examples are commercial simulations based on actual operating data from existing process units and pilot plant results from lab size units. The examples consider three process arrangements for the dehydrocyclodimerization of a 50,000 BPD LPG feedstream comprising a 50-50 blend of butane and propane.

In all three examples the dehydrocyclodimerization unit was operated in the same manner. The feed entered the reactor which operated at an average temperature of 55° C., a pressure of 600 kPag, and a liquid hourly space velocity of 2.6 hr.$^{-1}$ based upon the combined feed rate.

The dehydrocyclodimerization reaction zone contains a catalyst comprising about 49% of alumina containing phosphorus with a phosphorus content of about 21 wt. %, 50 wt. % ZSM-5 type zeolite, and 1.0 wt. % gallium, prepared by the method set forth in the example of U.S. Pat. No. 4,636,483. The light aliphatic hydrocarbon feedstock is converted into an aromatic hydrocarbon-containing product. The product analysis in lb/hr. is found in Table 1 and is the same for all three examples.

EXAMPLE 1

In conformance with prior art methods, the dehydrocyclodimerization reaction zone effluent is next directed in entirety to a hydrogenation reaction zone. The hydrogenation reaction zone consists of two separate reactors with a cooling means located therebetween to remove the exothermic heat of reaction produced in the first reactor from the intermediate hydrogenation reaction stream. Both reactors contain a fixed bed of hydrogenation catalyst. The hydrogenation catalyst comprised 0.75 wt. % platinum uniformly loaded upon a spherical alumina base and made essentially as disclosed herein. The first hydrogenation reactor operates at a pressure slightly below that of the outlet of the dehydrocyclodimerization reaction zone. In this case, the first reaction zone inlet pressure is 4.1 atmospheres gauge while the second reactor outlet pressure is 2.7 atmospheres gauge. The temperature of both reactors is controlled such that each reactor inlet temperature is 130° C. while each reactor outlet temperature does not exceed about 230° C. The hydrogenation reaction zone operates at a total liquid hourly space velocity of 2.5 hr.$^{-1}$.

The composition and properties for the effluent from the hydrogenation zone are shown in the Table. A cryogenic product recovery system is used in the arrangement of this example in order to obtain the high purity hydrogen for chemical consumption.

of deisohexanizer column. The process arrangement differs from that shown in Example 2 in that the effluent from the isomerization zone is stripped and then enters a deisohexanizer column. The process configuration for this example is the same as that shown in the Figure. Operating conditions for this example are essentially the same as those described for Example 2. Larger reactors were needed for the isomerization section of this example to accommodate the higher mass flow resulting from the recycle of the overhead from the deisohexanizer overhead. A large quantity of recycle was returned to the isomerization reactors from the deisohexanizer. The recycle of resulted in a combined feed ratio of 4. An isomerization section product stream is recovered overhead from the deisohexanizer column and combined with the aromatic stream in the manner described for Example 2. The composition and properties of the product stream is described in the Table.

The above examples show that both cases that use

TABLE 1

| Component | Dehydrocyclo-dimerization Effluent | | Hydrogenation Effluent | | Isomerization Effluent No Recycle | | Isomerization Effluent Deisohexanizer | |
|---|---|---|---|---|---|---|---|---|
| | lb/hr. | BPD | lb/hr. | BPD | lb/hr. | BPD | lb/hr. | BPD |
| Light Ends | | | | | 54 | — | 1,682 | — |
| $C_4$-$C_6$ Aliphatics | | | | | 36,816 | 3,845 | 52,421 | 5,519 |
| Cyclohexane | | | 52,830 | 4,627 | 16,770 | 1,469 | 4 | .5 |
| Benzene | 49,033 | 3,795 | 0 | 0 | 0 | 0 | 0 | 0 |
| Toluene | 92,720 | 7,283 | 92,720 | 7,283 | 92,720 | 7,283 | 92,720 | 7,283 |
| Xylenes | 52,338 | 4,133 | 52,338 | 4,133 | 52,338 | 4,133 | 52,338 | 4,133 |
| $A_9$-$A_{11}$ | 7,553 | 594 | 7,553 | 594 | 7,553 | 594 | 7,553 | 594 |
| Naphthalene | 10,726 | 738 | 10,726 | 738 | 10,726 | 738 | 10,726 | 738 |
| Total | 212,370 | 16,543 | 216,167 | 17,375 | 216,977 | 18,062 | 217,444 | 18,267 |
| RONC, Blend | | 116 | | 110 | | 107 | | 110 |
| Chemical $H_2$ | | — | | 3,797 | | 4,607 | | 5,074 |

EXAMPLE 2

This example uses the basic process of this invention. In this example the feedstream of Example 1 is treated in the same manner to obtain the dehydrocyclodimerization effluent described in the table which, after separation of hydrogen and light ends, is further separated such that benzene and lower boiling hydrocarbons are transferred to an isomerization section as an isomerization zone section feedstream and the remainder of the effluent having a boiling point above benzene is recovered as an aromatic stream. The isomerization section feedstream is passed to a two-stage stage isomerization zone having two separate reactors. Each reactor contains an alumina catalyst having 0.25 wt. % platinum and 5.5 wt. % chlorine. The feedstock was passed through the first reaction zone at a liquid hourly space velocity of 2.0, an outlet hydrogen to hydrocarbon molar ratio of 2, a pressure of about 3000 kPag and a temperature in a range of from 200°-260° C. Effluent from the first isomerization reactor is cooled and passed through the second isomerization reactor. For the most part the second isomerization reactor operates at substantially the same operating conditions as the first reaction zone with the exception of temperatures which are slightly lower and in a range of from 170°-230° C. The effluent from the isomerization zone was combined with the aromatic stream and a product stream having the composition shown in the Table was obtained.

EXAMPLE 3

This example shows the use of the process of this invention in a process arrangement that includes the use isomerization in place of the saturation of benzene yield a higher volume of liquid products. The effluent from the isomerization section of Example 2 has a lower research octane value than the hydrogenation effluent from Example 1; however, the additional volume of product obtained in Example 2 offsets its lower octane value in terms of overall product value. Moreover, the yield of products in Examples 2 and 3 includes substantial volumes of $C_4$-$C_6$ aliphatic hydrocarbons, especially $C_5$ and $C_6$ isoparaffins. These isoparaffins are not potential benzene producers, as is the cyclohexane in the product stream from the hydrogenation effluent of Example 1. Accordingly, the product stream from Examples 2 and 3 have the further advantage of providing a more environmentally acceptable liquid than that obtained from Example 1.

What is claimed is:

1. A process for producing isoalkane hydrocarbons from a feedstock comprising $C_2$-$C_6$ aliphatic hydrocarbons by the steps of:
   (a) passing a hydrocarbon feedstream comprising $C_2$-$C_6$ aliphatic hydrocarbons into a dehydrocyclodimerization reaction zone containing a dehydrocyclodimerization catalyst comprising a crystalline aluminosilicate zeolite, and a Group IIB-IVB metal component from the Periodic Table of the Elements at dehydrocyclodimerization reaction conditions including a temperature of from 350°-650° C., a pressure of from 10 to 2000 kPag and a liquid hourly space velocity of from 0.2 to 10.0 hr.$^{-1}$ to produce a dehydrocyclodimerization reaction zone effluent stream comprising hydrogen, methane, ethane, ethylene, $C_3$-$C_5$ aliphatic hydrocarbons, $C_6^+$ aliphatic hydrocarbons, and $C_6^+$ cyclic hydrocarbons;

(b) separating said dehydrocyclodimerization reaction zone effluent zone in a separation zone into an isomerization zone feed comprising $C_6$ and lower carbon number aliphatic and cyclic hydrocarbons and a cyclic hydrocarbon stream comprising $C_7$ and higher carbon number hydrocarbons;

(c) passing said isomerization zone feed into an isomerization reaction zone containing an isomerization catalyst comprising a Group VIII metal component on an alumina support and a chloride component where the isomerization reaction zone is operated at isomerization reaction conditions including a temperature of from 65°-290° C., a pressure of from 700 to 3100 kPag and a liquid hourly space velocity of from 1 to 12 hr.$^{-1}$ to produce an isomerization zone product stream that comprises isoalkane hydrocarbons and contains less hydrogen and cyclic hydrocarbons in comparison to the dehydrocyclodimerization reaction zone effluent;

(d) combining at least a portion of the isomerization zone product stream with said cyclic hydrocarbon stream comprising $C_7$ and higher carbon number hydrocarbons to produce a combined stream; and (e) recovering a high octane transportable hydrocarbon product comprising said combined stream.

2. The process of claim 1 further characterized in that the Group VIII metal component of the isomerization catalyst comprises platinum.

3. The process of claim 1 further characterized in that the isomerization reaction zone pressure is less than the dehydrocyclodimerization reaction zone pressure.

4. The process of claim 1 further characterized in that dehydrocyclodimerization reaction zone catalyst comprises a crystalline aluminosilicate zeolite component, a phosphorus-containing alumina component, and a metal component selected from the group comprising gallium, indium, thallium, tin, lead, and zinc.

5. The process of claim 4 further characterized in that the phosphorus-to-alumina molar ratio of the phosphorus containing alumina ranges from 1:1 to 1:100.

6. The process of claim 1 wherein said isomerization zone effluent is passed to a deisohexanizer to separate normal hexane and higher boiling hydrocarbons from said isomerization zone effluent stream, said normal $C_6$ and higher boiling hydrocarbons are recycled to said isomerization zone and the remainder of said isomerization effluent is combined with said cyclic hydrocarbon stream.

7. A process for producing isoalkane hydrocarbons from a feedstock comprising $C_2$-$C_6$ aliphatic hydrocarbons by the steps of:

(a) passing a $C_2$-$C_6$ aliphatic feedstream into a dehydrocyclodimerization reaction zone and into contact with a dehydrocyclodimerization catalyst comprising a ZSM-5 zeolite component, a phosphorus-containing alumina component, and gallium at dehydrocyclodimerization reaction zone conditions including a temperature of from 400°-600° C., a pressure of from 25 to 1000 kPag, and a liquid hourly space velocity of from 0.5 to 5.0 hr.$^{-1}$ to produce a dehydrocyclodimerization reaction zone effluent stream comprising hydrogen, methane, ethane, ethylene, $C_3$-$C_5$ aliphatic hydrocarbons, $C_6^+$ aliphatic hydrocarbons and $C_6^\pm$ cyclic hydrocarbons wherein said $C_6^\pm$ cyclic hydrocarbons include aromatic hydrocarbons;

(b) separating said dehydrocyclodimerization reaction zone effluent zone in a separation zone into an isomerization zone feed comprising $C_6$ and lower carbon number aliphatic and cyclic hydrocarbons and a cyclic hydrocarbon stream comprising $C_7$ and higher carbon number hydrocarbons;

(c) passing said isomerization feedstream and a hereinafter defined recycle stream into an isomerization reaction zone containing an isomerization catalyst comprising platinum on alumina and a chloride component all at isomerization reaction conditions including a temperature of from 100°-260° C., a pressure of from 700 to 3100 kPag and a liquid hourly space velocity of from 1 to 8 hr.$^{-1}$ to produce an isomerization reaction zone product stream that contains fewer cyclic hydrocarbons and hydrogen than the dehydrocyclodimerization reaction zone effluent (d) passing the isomerization product stream to a deisohexanizer to separate said isomerization zone product stream into said recycle stream comprising normal hexane and higher boiling hydrocarbons and an isoalkane product stream comprising $C_6$ isoalkanes and lower boiling hydrocarbons;

(e) combining said cyclic hydrocarbon stream comprising $C_7$ and higher carbon number hydrocarbons with said isoalkane product stream; and, (f) recovering a high octane transportable product comprising said combined cyclic hydrocarbon stream and said isoalkane stream.

8. The process of claim 7 further characterized in that essentially all the benzene components in the dehydrocyclodimerization reaction zone effluent stream are converted into aliphatic hydrocarbons in the isomerization reaction zone.

9. The process of claim 7 further characterized in that the dehydrocyclodimerization reaction zone contains a moving bed of catalyst.

10. The process of claim 7 further characterized in that the gallium component of the dehydrocyclodimerization catalyst is present in an amount ranging from 0.5 to 5.0 wt. %.

11. The process of claim 7 further characterized in that the isomerization reaction zone comprises at least two separate reactors.

* * * * *